US011123902B2

(12) United States Patent
Endle et al.

(10) Patent No.: US 11,123,902 B2
(45) Date of Patent: Sep. 21, 2021

(54) METHOD OF MAKING A PERSONAL PROTECTIVE ARTICLE

(71) Applicant: 3M INNOVATIVE PROPERTIES COMPANY, St. Paul, MN (US)

(72) Inventors: James P. Endle, New Richmond, WI (US); Jeffrey L. Hamer, Springville, IN (US); Alan R. Seville, Indianapolis, IN (US); Kenneth F. Teeters, Zionsville, IN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 380 days.

(21) Appl. No.: 16/103,194

(22) Filed: Aug. 14, 2018

(65) Prior Publication Data

US 2018/0361633 A1 Dec. 20, 2018

Related U.S. Application Data

(60) Division of application No. 14/601,356, filed on Jan. 21, 2015, now Pat. No. 10,065,344, which is a (Continued)

(51) Int. Cl.
| | |
|---|---|
| B29C 44/12 | (2006.01) |
| C08J 9/10 | (2006.01) |
| C08J 9/32 | (2006.01) |
| A61F 11/08 | (2006.01) |
| B29C 44/34 | (2006.01) |
| B29L 31/00 | (2006.01) |
| B29K 25/00 | (2006.01) |
| B29L 9/00 | (2006.01) |
| B29L 31/48 | (2006.01) |

(52) U.S. Cl.
CPC .............. *B29C 44/12* (2013.01); *A61F 11/08* (2013.01); *B29C 44/1266* (2013.01); *B29C 44/3484* (2013.01); *C08J 9/105* (2013.01); *C08J 9/32* (2013.01); *A61F 2011/085* (2013.01); *B29K 2025/04* (2013.01); *B29L 2009/00* (2013.01); *B29L 2031/4842* (2013.01); *B29L 2031/768* (2013.01); *C08J 2203/04* (2013.01); *C08J 2203/184* (2013.01); *C08J 2203/22* (2013.01); *C08J 2353/02* (2013.01)

(58) Field of Classification Search
CPC .. B29C 44/0407; B29C 44/06; B29C 44/1271
See application file for complete search history.

(56) References Cited

U.S. PATENT DOCUMENTS 2,538,339 A 1/1951 Thomas
3,736,929 A 6/1973 Mills
(Continued)

FOREIGN PATENT DOCUMENTS

DE 10 2010 021473 2/2012
EP 108728 11/1983
(Continued)

*Primary Examiner* — James Sanders
(74) *Attorney, Agent, or Firm* — Katherine M. Scholz; Dena M. Ehrich

(57) ABSTRACT

A method of making personal protective equipment, such as a push-in earplug, is disclosed. The method includes the steps of covering a substrate with an outer layer that includes an unactivated foaming agent, positioning at least a portion of the outer layer in a mold, and activating the foaming agent such that a portion of the outer layer expands.

9 Claims, 4 Drawing Sheets

Related U.S. Application Data continuation of application No. 13/547,189, filed on Jul. 12, 2012, now Pat. No. 8,968,613.

(56) References Cited

U.S. PATENT DOCUMENTS

| | | | |
|---|---|---|---|
| 4,434,794 A | 3/1984 | Leight |
| 4,724,922 A | 2/1988 | Kalayjian |
| 5,188,123 A | 2/1993 | Gardner |
| 5,333,622 A | 8/1994 | Casali |
| 5,573,015 A | 11/1996 | Williams |
| 5,609,164 A | 3/1997 | Dyrud |
| 5,792,998 A | 8/1998 | Gardner |
| 5,799,658 A | 9/1998 | Falco |
| 5,811,742 A | 9/1998 | Leight |
| 5,988,313 A | 11/1999 | Håkansson |
| 6,006,857 A | 12/1999 | Leight |
| 6,241,042 B1 | 6/2001 | Falco |
| 6,345,684 B1 | 2/2002 | Leight |
| 6,408,981 B1 | 6/2002 | Smith |
| 6,568,395 B2 | 5/2003 | Tiemens |
| 6,586,483 B2 | 7/2003 | Kolb |
| 6,659,103 B2 | 12/2003 | Tiemens |
| 6,695,093 B1 | 2/2004 | Falco |
| 6,981,504 B2 | 1/2006 | Jenkins |
| 7,096,872 B2 | 8/2006 | Ligon, Sr. |
| 7,192,544 B2 | 3/2007 | Jenkins, Jr. |
| 7,220,372 B2 | 5/2007 | Woo |
| 7,464,786 B2 | 12/2008 | Falco |
| 7,475,686 B2 | 1/2009 | Knauer |
| 7,510,046 B2 | 3/2009 | Doty |
| 7,727,433 B2 | 6/2010 | Knauer |
| 7,731,487 B2 | 6/2010 | Knauer |
| 7,837,005 B2 | 11/2010 | Killion |
| 7,886,744 B2 | 2/2011 | Knauer |
| 8,061,472 B2 | 11/2011 | Tiemens |
| 8,118,031 B2 | 2/2012 | Seville |
| 8,969,613 B2 | 3/2015 | Endle |
| 10,065,344 B2 | 9/2018 | Endle |
| 2002/0114927 A1 | 8/2002 | Brossman |
| 2003/0029459 A1 | 2/2003 | Tiemens |
| 2004/0045558 A1 | 3/2004 | Taylor |
| 2004/0068848 A1 | 4/2004 | Ausen |
| 2005/0039761 A1 | 2/2005 | Jenkins |
| 2006/0138691 A1 | 6/2006 | Knauer |
| 2006/0202375 A1 | 9/2006 | Jenkins, Jr. |
| 2007/0142486 A1 | 6/2007 | Limerkens |
| 2009/0071487 A1 | 3/2009 | Keady |
| 2010/0300460 A1 | 12/2010 | Falco |
| 2010/0307861 A1 | 12/2010 | Tiemens |

FOREIGN PATENT DOCUMENTS

| | | |
|---|---|---|
| FR | 2230336 | 5/1974 |
| TW | 200918026 | 10/1996 |
| WO | WO 1998/06362 | 2/1988 |
| WO | WO 92/00049 | 1/1992 |
| WO | WO 2000/44821 | 8/2000 |
| WO | WO 2002/43633 | 6/2002 |
| WO | WO 2007/044766 | 4/2007 |
| WO | WO 2010/134554 | 11/2010 |

METHOD OF MAKING A PERSONAL PROTECTIVE ARTICLE

TECHNICAL FIELD

This description relates to a method of making an article, in particular a method of making a personal protective article having a substrate including a first material, and an outer layer including a second material.

BACKGROUND

The use of hearing protective and noise attenuating devices are well known, and various types of devices have been considered. Such devices include earplugs and semi-aural devices partially or completely constructed of foam or rubber materials that are inserted into, or placed over, the ear canal of a user to physically obstruct the passage of sound waves into the inner ear.

Compressible or "roll-down" type earplugs generally comprise a compressible, resilient body portion and may be made of suitable slow recovery foam materials. The earplug may be inserted into the ear canal of a user by first rolling it between fingers to compress the body portion, then pushing the body portion into the ear canal, and subsequently allowing the body portion to expand to fill the ear canal.

Push-in type earplugs have also been considered, and may include a compressible attenuating portion and a stiff portion that extends from the attenuating portion. To insert a push-in type earplug, the user grasps the stiff portion and pushes the attenuating portion into the ear canal with an appropriate level of force. The attenuating portion compresses as it is accommodated in the ear canal. Push-in earplugs may allow the earplug to be quickly and easily inserted in an ear canal, and may promote hygiene by minimizing contact with the attenuating portion of the earplug prior to insertion.

Although push-in earplugs exhibit desirable characteristics in various applications, they may be costly and may pose difficult manufacturing challenges.

SUMMARY

Glossary

"Mold" means a hollow form that may or may not impart a shape on a component placed in the hollow form.

"Thermally bonded" means a state in which molecules of two materials or surfaces have diffused into the material or surface of the other when in a molten phase such that a bond is formed. Chemical bonding is absent or does not provide the primary source of bonding between thermally bonded materials or surfaces.

"Thermoplastic" means a polymer that can be repeatably heated and re-shaped and will retain its shape upon cooling.

"Thermoset" means a polymer that may be irreversibly cured.

"Unactivated" when referring to a foaming agent means that the foaming agent can be further activated to facilitate the formation of gas or cells in a material.

In one embodiment of the present description, a method of making an earplug is disclosed, including the steps of covering an elongate core with an outer layer, wherein the elongate core includes a first material and the outer layer includes a second material, the second material includes an unactivated foaming agent. The method further includes steps of positioning at least a portion of the outer layer and the elongate core in a mold and activating the foaming agent of at least a portion of the outer layer to form a sound attenuating portion and a stem portion bonded to the elongate core. In another embodiment, the sound attenuating portion may have a first average density $\rho 1$ and the stem portion has a second average density $\rho 2$ and $|\rho 2 > 1.2 \rho 1|$, or $|\rho 2 > 1.5 \rho 1|$. The second material includes an unactivated chemical foaming agent and/or an unactivated expandable sphere foaming agent. In various exemplary embodiments, the second material comprises one or more of a thermoplastic, styrene-ethylene-butylene-styrene (SEBS), thermoset polymers, and EPDM rubbers. 20. The outer layer is a contiguous layer and is thermally bonded to the elongate core.

In another embodiment, the mold includes a first cavity that limits expansion of the outer layer, and the first cavity is in the form of a sound attenuating portion. The mold further comprises a second cavity in the form of a stem portion. In a further embodiment, at least a portion of the step of activating the foaming agent occurs while the first cavity is oriented below the second cavity. The step of activating the foaming agent comprises applying heat to at least a portion of the outer layer. In another exemplary embodiment, the method includes the step of extruding the first material to form the elongate core. The step of covering the elongate core comprises a step selected from the group consisting of extruding, laminating, molding, spraying and dipping.

In another embodiment of the present description, a method of making an earplug is disclosed, including the steps of extruding an elongate core including a first material, covering the elongate core with an outer layer including a second material, the second material including an unactivated expandable sphere foaming agent, an unactivated chemical foaming agent, and styrene-ethylene-butylene-styrene (SEBS), positioning at least a portion of the outer layer and the elongate core in a mold, and applying heat to at least a portion of the outer layer such that at least a portion of the outer layer expands such that the outer layer includes a sound attenuating portion and a stem portion bonded to the elongate core. In an exemplary embodiment, the sound attenuating portion has a first average density $\rho 1$ and the stem portion has a second average density $\rho 2$ and $|\rho 2 > 1.2 \rho 1|$, and the outer layer is thermally bonded to the elongate core.

In a further embodiment of the present description, a method of making an article is disclosed, including the step of covering a substrate with an outer layer. The substrate includes a first material and the outer layer includes a second material, the second material includes an unactivated expandable sphere foaming agent. The method includes the further steps of positioning at least a portion of the outer layer in a mold, and applying heat at least a portion of the outer layer such that at least a portion of the outer layer expands and conforms to a shape of the mold and the outer layer is bonded to the substrate. In an exemplary embodiment, the second material comprises an unactivated chemical foaming agent, and a thermoplastic, and the outer layer is thermally bonded to the substrate.

U.S. Patent Publication 2014/0014121 addresses the structure and configuration of a push-in earplug, and U.S. Pat. No. 8,679,607, addresses an article for forming a device or component, and are incorporated herein by reference.

DETAILED DESCRIPTION

An earplug that provides hearing protection for a user, and a method of making an earplug, is provided in the following description. An earplug according to the present description includes a relatively stiff elongate core covered, directly or indirectly, by a relatively soft outer layer. The outer layer includes a compressible sound attenuating portion that may be inserted into the ear canal of a user, and stem portion that may be grasped by a user to handle the earplug. Such an earplug may be easily inserted into an ear canal without first requiring that the sound attenuating portion be compressed or "rolled down." The present description further provides a method of making an earplug that minimizes difficult and expensive manufacturing techniques. The method may include the steps of covering a substrate, such as an elongate core, with an outer layer that includes an unactivated foaming agent, and activating the foaming agent such that at least a portion of the outer layer expands into a desired shape.

Figure 1:
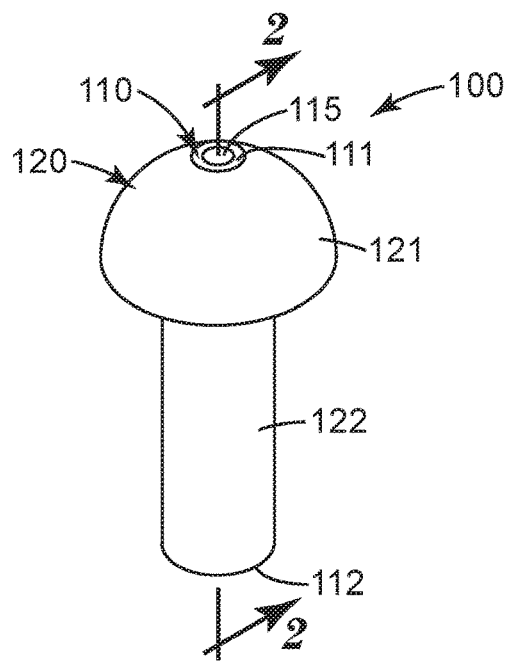
FIG. 1 is a perspective view of a push-in earplug according to the present description.
Figure 2:
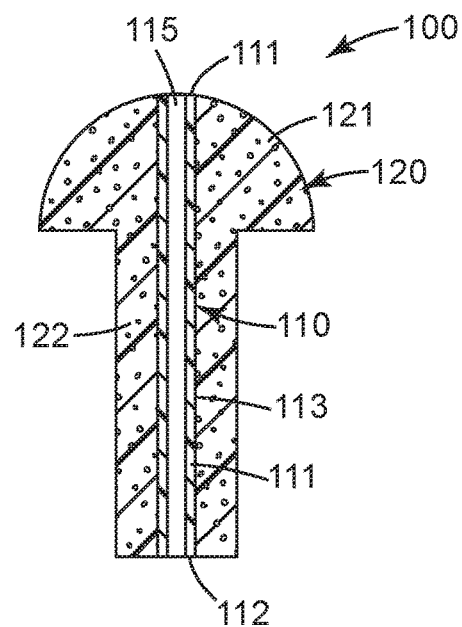
FIG. 2 is a cross-sectional view of a push-in earplug according to the present description.
Figure 3A:
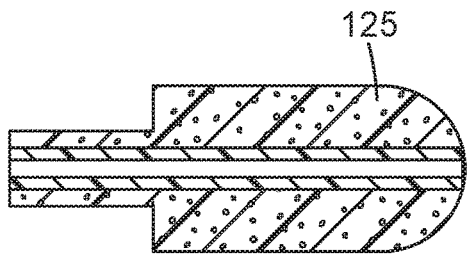
FIGS. 3A-3D are cross-sectional views of exemplary push-in earplugs according to the present description showing sound attenuating portions having various exemplary shapes.
Figure 3B:
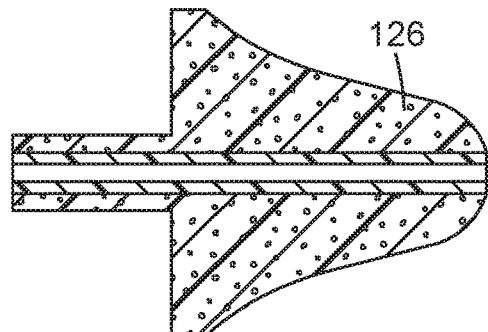
Figure 3C:
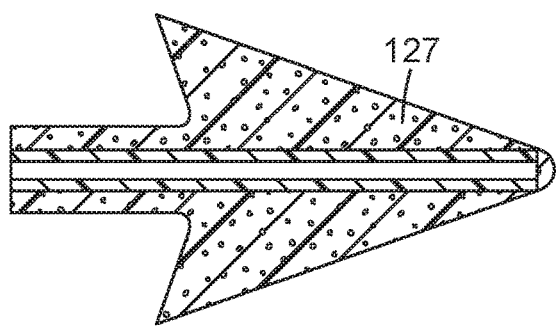
Figure 3D:
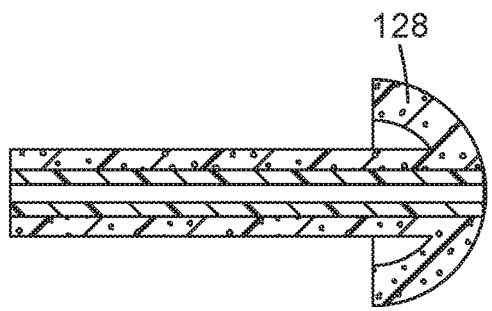

FIGS. 1 and 2 show a push-in earplug 100 according to the present description. Earplug 100 includes an elongate core 110 made of a first material and having first and second ends 111 and 112, and an outer major surface 113. Earplug 100 further includes an outer layer 120 made of a second material and bonded, directly or indirectly, to at least a portion of outer major surface 113 of elongate core 110. Outer layer 120 includes a sound attenuating portion 121 for at least partial insertion into the ear canal of a user, for example, and a stem portion 122 having a smaller diameter and greater average density than sound attenuating portion 121. In some embodiments, a channel 115 extends completely or partially through elongate core 110 between first and second ends 111 and 112.

During insertion of earplug 100, stem portion 122 and elongate core 110 serve as a handle which may be gripped by a user. Earplug 100, and specifically sound attenuating portion 121, is brought proximate to the user's ear and inserted into the ear canal. Sound attenuating portion 121 compresses as it is positioned, and elongate core 110 provides sufficient stiffness to facilitate insertion. In use, sound attenuating portion 121 is positioned substantially within an ear canal to block the passage of sound and stem portion 122 extends outwardly from the ear canal to provide a handle to remove the earplug.

Elongate core 110 provides a substrate onto which outer layer 120 may be covered, directly or indirectly, and facilitates insertion of earplug 100 into the ear canal of a user. In an exemplary embodiment, elongate core 110 is made of a first material that exhibits greater rigidity or stiffness than outer layer 120, yet is soft enough to be comfortable and safe for a user. Elongate core 110 provides sufficient rigidity that earplug 100 may be positioned for use at least partially in the ear of a user by pushing sound attenuating portion 121 into the ear canal with an appropriate force. That is, a sufficiently stiff elongate core 110 combined with an appropriate outer layer 120 allows earplug 100 to be positioned for use at least partially in the ear of a user without the need to first compress or "roll down" sound attenuating portion 121. Direct insertion without the need to first compress or "roll down" sound attenuating portion 121, for example, promotes hygiene by limiting contact with sound attenuating portion 121 prior to placement in the ear. Elongate core 110 also exhibits an appropriate level of flexibility such that it may slightly deform to the contours of the ear canal when positioned for use.

Elongate core 110 is made from one or more materials that can suitably bond to, and are otherwise compatible with, the material of outer layer 120 or one or more intermediate layers. In an exemplary embodiment, elongate core 110 is made from a blend of polypropylene and styrene-ethylene-butylene-styrene (SEBS), such as TUFPRENE available from S&E Specialty Polymers, LLC. of Lunenburg, Mass. Other suitable materials include SANTOPRENE 101-90, available from Exxon Mobile Corporation, and other materials exhibiting appropriate stiffness such that attenuating portion 121 of earplug 100 may be easily inserted into the ear canal of a user.

Elongate core 110 may be made of one or more materials having a specified hardness. In various exemplary embodiments, the hardness of at least a portion of elongate core 110 is between 50 and 100 Shore A, or between 70 and 90 Shore A, or about 80 Shore A. A desired hardness may depend on the dimensions of elongate core 110 such that elongate core 110 exhibits a desired stiffness.

In an exemplary embodiment, elongate core 110 has a circular cross-section that is substantially uniform at any location between first and second ends 111 and 112 such that elongate core 110 exhibits a generally cylindrical shape. A circular cross section may minimize edges that may cause discomfort by contacting portions of a user's ear. In various other exemplary embodiments, elongate core may have a triangular, square, or other suitable cross-section, or may have a cross-section that varies along the length of earplug 100. Outer major surface 113 may have a knurled, grooved, or otherwise textured surface. Such a surface may increase the surface area that contacts outer layer 120 or an intermediate layer such that a robust bond is created. In some exemplary embodiments, elongate core 110 includes multiple concentric layers, such as a layer to provide a desired stiffness and a layer that facilitates a robust bond with the outer layer, or that provides other desired characteristics.

In some exemplary embodiments, elongate core 110 is hollow and in the form of a tube defining a channel 115. Earplug 100 having a hollow elongate core 110 may be manufactured such that components of a receiver or of a communication system may be attached to the earplug. Alternatively or in addition, channel 115 may accommodate one or more filters or other passive hearing elements to provide an attenuation curve having a desired shape. For example, filters positioned in channel 115 may cause non-linear attenuation of high level impulses produced by explosions, gunfire, or the like. Channel 115 may also provide a recess that a cord may be attached to, such that first and second earplugs may be joined, or that ends of a headband may be attached to in a semi-aural hearing protector.

Earplug 100 further includes an outer layer 120 substantially covering, directly or indirectly, elongate core 110 and including sound attenuating portion 121 and stem portion 122. In an exemplary embodiment, outer layer 120 substantially surrounds outer major surface 113 of elongate core 110 and extends from first end 111 to second end 112 of elongate core 110. In some embodiments, outer layer 120 is a contiguous layer such that portions of sound attenuating portion 121 contact portions of stem portion 122. First and second ends 111 and 112 of elongate core 110 may be at least partially exposed, and elongate core 110 may be colored similarly or dissimilarly from the color of outer layer 120 to hide or exhibit the presence of elongate core 110. Sound attenuating portion 121 is positioned near first end 111 of elongate core 110 and is shaped to be accommodated in an ear canal of a user. In an exemplary embodiment, sound attenuating portion 121 has a substantially domed or hemispherical shape, and has a diameter at its widest point that is greater than a diameter of stem portion 122. In various other embodiments shown in FIGS. 3A through 3D, for example, sound attenuating portions 125, 126, 127, 128, respectively, may be bullet-shaped, bell-shaped, cone-shaped, mushroom-shaped, or otherwise shaped to provide a desired fit or to suit a particular application.

Outer layer 120 is made of soft and pliable foam, rubber, polymer, or other suitable material that may be comfortably positioned in an ear canal of a user. In an exemplary embodiment, outer layer 120 is made of an SEBS, such as MONPRENE MP1900 available from Teknor Apex of Pawtucket, R.I.. Other suitable materials include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art that can be formulated to exhibit an appropriate hardness range. In an exemplary embodiment, the materials of elongate core 110 and outer layer 120 are selected such that the primary source of bonding between elongate core 110 and outer layer 120, directly or indirectly, is thermal bonding. An additional adhesive is not required to bond elongate core 110 and outer layer 120, and such an adhesive is not present between elongate core 110 and outer layer 120 in an exemplary embodiment. In some exemplary embodiments, outer layer 120 includes multiple concentric layers, such as a layer to provide desired characteristics for contacting an ear canal of a user and a layer that facilitates a robust bond with the elongate core, or layers that provides other desired characteristics.

The material of outer layer 120 may be selected to control the friability of the outer layer 120 such that it may not easily be broken or disintegrate during use. The friability of an earplug may be controlled in part by selecting a material having an appropriate molecular weight, with higher molecular weight generally resulting in a less friable earplug. In an exemplary embodiment, outer layer 220 includes an SEBS having a molecular weight between 100,000 Daltons and 200,000 Daltons, as measured by gel permeation chromatography analysis as known in the art, such as according to ASTM D6474-99.

The density of outer layer 120 can be controlled during manufacturing to provide a specified density as desired for a particular application. Outer layer 120 may exhibit a density that varies by thickness, for example, such that outer layer 120 has an integral outer skin that is more dense than the remainder of outer layer 120. Such a skin may be present on one or both of sound attenuating portion 121 and stem portion 122. Alternatively, sound attenuating portion 121 or stem portion 122 may have a substantially uniform density. In an exemplary embodiment, irrespective of the presence of an integral outer skin or varying densities within sound attenuating portion 121 or stem portion 122, sound attenuating portion 121 has a first average density $\rho 1$ and the stem portion has a second average density $\rho 2$. First and second average densities $\rho 1$ and $\rho 2$ can be found by averaging the densities at each location of sound attenuating portion 121 or stem portion 122. Without being bound by theory, the average density is believed to provide an indication of the ability of sound attenuating portion 121 or stem portion 122 to compress or otherwise conform when subjected to an external force. The first average density $\rho 1$ of sound attenuating portion 121 is selected such that sound attenuating portion may provide a comfortable fit by conforming to the ear canal of a user, while providing a desired level of sound attenuation. In various exemplary embodiments, the first average density $\rho 1$ of a sound attenuating portion 121, comprising a foamed SEBS for example, is between 100 $kg/m^3$ and 180 $kg/m^3$, or 110 $kg/m^3$ and 160 $kg/m^3$, or may be about 125 $kg/m^3$. The second average density $\rho 2$ of stem portion 122 is greater than the first average density $\rho 1$, and in various exemplary embodiments is between 200 $kg/m^3$ and 300 $kg/m^3$, 225 $kg/m^3$ and 275 $kg/m^3$, or may be about 250 $kg/m^3$. Accordingly, in various exemplary embodiments, the second average density $\rho 2$ of stem portion 122 of outer layer 120 is greater than 1.2, 1.5, 2 or more times the first average density $\rho 1$ of sound attenuating portion 121 of outer layer 120.

Earplug 100 may be formed in a multiple step process. In an exemplary embodiment, earplug 100 is formed in a process that involves an intermediate state in which outer layer 120 is covered around elongate core 110, directly or indirectly, to result in a pre-formed hearing protection device such as pre-form 130, but does not yet include sound attenuating portion 121. In the intermediate state shown in FIG. 4, outer layer 120 of pre-form 130 includes an unactivated foaming agent. In an exemplary embodiment, the unactivated foaming agent includes an expandable sphere foaming agent that includes thermoplastic spheres, for example, that include a shell encapsulating a hydrocarbon or other appropriate gas that expands when exposed to heat or other activation source. Expansion of the thermoplastic shell results in an increased volume and reduced density of the material of outer layer 120. The unactivated foaming agent may also be a chemical foaming agent that includes an expandable material that is self-contained or otherwise not contained by an expandable sphere. Activation of such a foaming agent causes the expandable material to expand creating voids or gaps in the material of the outer layer. In an exemplary embodiment, the outer layer 120 of pre-form 130 includes an unactivated expandable sphere foaming agent and an unactivated chemical foaming agent. Activation of the foaming agent or agents present in outer layer 120, and the associated expansion of outer layer 120, can be controlled to provide an earplug 100 having a sound attenuating portion 121 and stem portion 122 exhibiting a desired shape, density, hardness, and other desired characteristics. The presence of both an expandable sphere foaming agent and a chemical foaming agent may assist in providing sufficient structure and expansion such that the outer layer may be appropriately formed during activation, while reducing the hardness of the outer layer from a level that would otherwise result if only an expandable sphere foaming agent were used. Some or all of a gas generated by a chemical foaming agent may escape during activation such that some or all of the gas is not present in the outer layer after activation. Some or all of an expandable sphere foaming agent may remain in the outer layer of a final earplug such that a final earplug may include thermoplastic spheres. In an exemplary embodiment, outer layer 120 of earplug 100 includes between 1% and 5% weight, and may include approximately 3% weight, of the foaming agent or remnants of the foaming agent.

Figure 4:
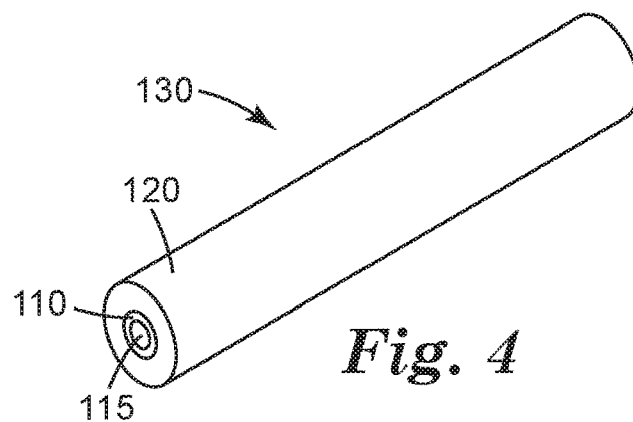
FIG. 4 is a perspective view of a pre-form that includes an elongate core and an outer layer in an intermediate state of an exemplary method of making an earplug.

In the intermediate state shown in FIG. 4, pre-form 130 may be cut to the desired length of earplug 100, may be cut to an extended length sufficient for subsequent formation of many earplugs, or may remain uncut such that activation of outer layer 120 occurs prior to cutting as described below with reference to FIG. 8. Pre-form 130 having an extended length may facilitate handling for subsequent processing and activation of the foaming agent. In an exemplary embodiment, pre-form 130 is cut to an extended length that can be subsequently cut and activated to yield a desired quantity of earplugs 100. An extended pre-form 130 may be coiled or otherwise shaped for ease in transporting or handling.

The present description provides a method of making personal protective equipment, such as earplug 100 described above. An exemplary method includes steps of covering a substrate with an outer layer, and applying heat to at least a portion of the outer layer such that at least a portion of the outer layer expands. Expansion of the outer layer occurs due to activation of a foaming agent present in the material of the outer layer and can be controlled by positioning at least a portion of the outer layer in a mold prior to expansion. Portions of the outer layer may be confined by the shape of the mold as the outer layer expands, or are shielded from heat to limit activation of the foaming agent.

The method described herein is suitable not only for manufacturing earplugs, but also for manufacturing other types of hearing protection devices and components for other personal protective equipment, as well as other molded or formed parts suitable for other applications. For example, the present method provides a process for making a seal for a facepiece of a respiratory protection device that can be foamed to provide a desired shape and density. Other exemplary applications include the manufacture of ear muffs, respirators, eyewear, other personal protective equipment, components of such personal protective equipment, and other applications.

An exemplary method of making a push-in earplug according to the present description includes the steps of covering an elongate core, directly or indirectly, with an outer layer comprising an unactivated foaming agent, and activating the foaming agent of at least a portion of the outer layer to form a sound attenuating portion and a stem portion bonded, directly or indirectly, to the elongate core.

Figure 5:
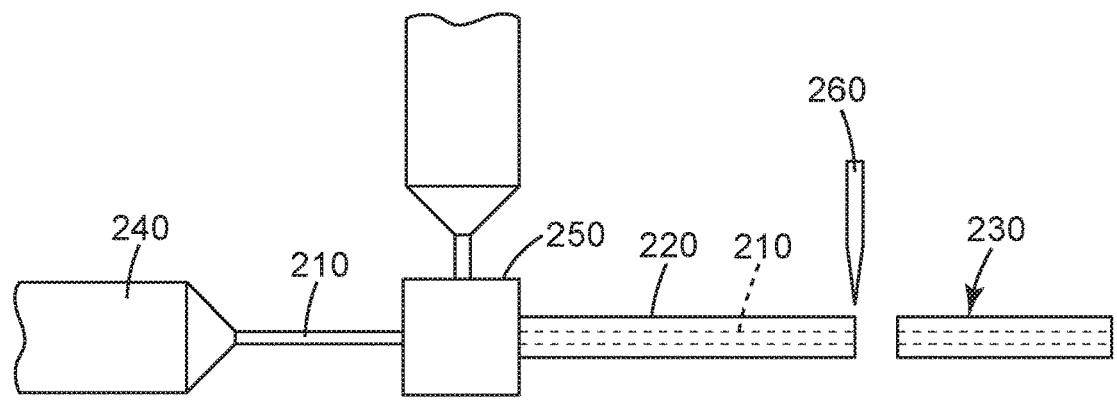
FIG. 5 is a schematic representation of an exemplary manufacturing process according to the present description.

FIG. 5 shows a schematic of an exemplary method of making an earplug 200 according to the present description. An extended elongate core 210 is formed by extruding a first material through a first die 240 and drawing the first material to an appropriate diameter. As described above, the elongate core may be solid or may include a longitudinal channel extending through all or a portion of elongate core 210, and may include one or more concentric layers having differing characteristics. The first material may be cooled such that it remains stable in subsequent steps of the manufacturing process. The magnitude of temperature change may depend on the materials used and the desired characteristics of the final product. In an exemplary embodiment, elongate core 210 is cooled as necessary such that it exhibits a temperature at a point before being covered by second die 250 that is lower than an activation or curing temperature of outer layer 220. Prior to being covered, elongate core 210 has an extended length and is not yet cut to the desired length for an earplug.

In the embodiment shown in FIG. 5, elongate core 210 is covered, directly or indirectly, with an outer layer 220 comprising a second material, by second die 250. Second die 250 may be a co-extrusion die or other suitable die as known in the art. In an exemplary embodiment, the second material comprises a thermoplastic and one or more unactivated foaming agents. Outer layer 220 is applied to elongate core 210 while remaining at a temperature below an activation temperature of the unactivated foaming agents. In an exemplary embodiment, the second material includes SEBS and a foaming agent having an activation temperature between 100° C. and 205° C., 120° C. and 190° C., or of about 170° C. Other suitable materials include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art. In embodiments in which outer layer 220 includes a second material having a rubber or thermoset polymer, outer layer 220 may be applied at a temperature below a vulcanizing or curing temperature of the rubber or thermoset polymer. In such an embodiment, outer layer 220 may include an unactivated foaming agent and an uncured or partially cured rubber or thermoset polymer that can be subsequently activated and cured, respectively, with heat or other suitable activation or curing process.

The weight percentage of foaming agent in outer layer 220 when initially applied to elongate core 210 may be selected based on the type of thermoplastic or other material used and the desired final shape, density, hardness or other characteristics of sound attenuating portion 221. In an exemplary embodiment, outer layer 220 has an initial composition of between 90% and 99.5% SEBS and between 10% and 0.5% of an appropriate unactivated foaming agent, or of approximately 93% SEBS and 7% of an unactivated expandable sphere foaming agent, such as EXPANCEL 930 DU 120, EXPANCEL 920 DU 120, both available from Eka Chemicals AB of Sundsvall, Sweden. In other exemplary embodiments, outer layer 220 has an initial composition including an unactivated chemical foaming agent such as oxybis benzene sulfonyl hydrazide (OBSH) available from Biddle Sawyer Corp. of New York, N.Y. The presence of a chemical foaming agent such as an OBSH foaming agent may yield a sound attenuating portion having a lower hardness value than a sound attenuating portion formed of an outer layer including an expandable sphere foaming agent such as EXPANCEL as the only foaming agent. In an exemplary embodiment, outer layer 220 includes an unactivated expandable sphere foaming agent and an unactivated chemical foaming agent. The presence of both an expandable sphere foaming agent and a chemical foaming agent may assist in providing sufficient structure such that the outer layer may be appropriately formed and that may not be present with a chemical foaming agent alone, while reducing the hardness of the outer layer from a level that would otherwise result if only an expandable sphere foaming agent were used. Accordingly, the combination of a chemical foaming agent and an expandable sphere foaming agent may result in an outer layer having a hardness level appropriate for a desired application, such as for insertion into an ear canal. In an exemplary embodiment, outer layer 220 when initially applied may include between approximately 0.5% weight and 3% weight of an unactivated chemical foaming agent, or of approximately 2% weight of an unactivated chemical foaming agent, and between approximately 0.5% weight and 9.5% weight of an unactivated expandable sphere foaming agent, or of approximately 2% weight of an unactivated expandable sphere foaming agent. Outer layer 220 may also include other suitable foaming agents, or various combinations of EXPANCEL foaming agents, OBSH foaming agents, and other suitable foaming agents. Outer layer 220 may further include pigment to impart a desired color, antioxidants, UV stabilizers, and oils or waxes to aid in extrusion and mold release as known in the art.

In some exemplary embodiments, outer layer 220 is in a molten state when covered over elongate core 210. As a result, molecules of outer layer 220 and elongate core 210, or of one or more intermediate layers, are believed to diffuse into the material or surface of each other and a thermal bond is formed. When the materials or surfaces cool and solidify, outer layer 220 remains thermally bonded, directly or indirectly, to elongate core 210. In an exemplary embodiment, significant chemical bonding is absent such that the primary source of bonding between elongate core 210 and outer layer 220 is thermal bonding. In other exemplary embodiments, outer layer 220 contacts elongate core 210 or one or more intermediate layers when covered over elongate core 210 but no significant bond is formed between outer layer 220 and elongate core 210 or one or more intermediate layers. Upon activation and/or curing of outer layer 220, a thermal bond may be formed, directly or indirectly, between outer layer 220 and elongate core 210.

In other exemplary embodiments, elongate core 210 may be covered with outer layer 220, or one or more intermediate layers, by laminating, molding, spraying, dipping, or other suitable process as known in the art as an alternative or in addition to second die 250. Such steps may occur before or after elongate core 210 is cut to a desired length. Regardless of the process used, the temperature of outer layer 220 should remain below the activation temperature of the foaming agent(s) such that the foaming agent(s) remain unactivated during the covering process. In the event that an uncured or partially cured material is included in outer layer 220, such as an EPDM rubber or thermoset polymer, the temperature of outer layer 220 should remain below the curing temperature of the material.

In an exemplary embodiment, elongate core 210 covered by outer layer 220 is cut to the length of a desired earplug with cutter 260. The result is pre-form 230 having elongate core 210 and outer layer 220 in which outer layer 220 includes an unactivated foaming agent that may be subsequently activated to create an earplug having a sound attenuating portion 221 and a stem portion 222.

Cutter 260 may cut pre-form 230 to a desired length of earplug 200, or to an extended length sufficient for subsequent formation of many earplugs. In an exemplary embodiment, pre-form 230 is cut to an extended length that can be subsequently cut and activated, or vice versa, to yield a desired quantity of earplugs 200. An extended pre-form 230 may be coiled or otherwise shaped for ease of handling or transportation.

In an exemplary embodiment, the unactivated foaming agent present in outer layer 220 includes thermoplastic spheres encapsulating a hydrocarbon or other expandable material. Application of an appropriate amount of heat causes the thermoplastic shell and hydrocarbon to expand. In other exemplary embodiments, the foaming agent includes, alone or in combination with an expandable sphere foaming agent, an expandable material that is self-contained or not otherwise encapsulated, and that produces gas when exposed to heat or other activation source. If left unrestrained, activation of the foaming agent(s) creates cells in outer layer 220, ultimately increasing volume and decreasing density of outer layer 220. Expansion of outer layer 220 can be controlled by the thickness and composition of outer layer 220, selective application of heat, catalyst, or other activation source, and/or by placing at least a portion of pre-form 230 in a mold to limit expansion of outer layer 220 as the foaming agent is activated.

Figure 6A:
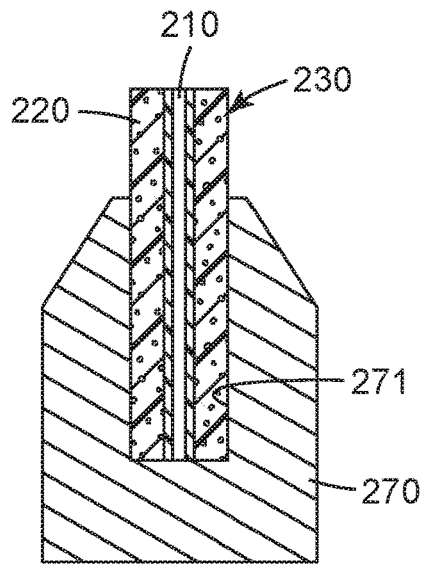
FIGS. 6A and B are cross-sectional views of an example of a mold used in an exemplary embodiment of the present description.
Figure 6B:
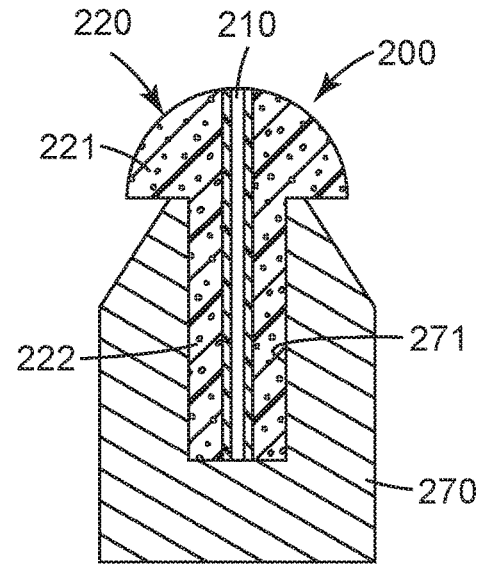

In the exemplary method shown in FIGS. 6A and 6B, mold 270 is used to control expansion of outer layer 220. Mold 270 includes a first cavity 271 in the form of a stem portion that receives a portion of pre-form 230. Pre-form 230 may be cut to the length of a desired earplug 200 prior to being placed in mold 270. Alternatively, pre-form 230 may be of an extended length and may be cut to length after being inserted into mold 270. Cutting pre-form 230 after insertion into mold 270 may facilitate handling and insertion. Heat is applied to the exposed portion of pre-form 230 to raise the temperature of outer layer 220 at least to an activation temperature of a foaming agent present in outer layer 220 and cause outer layer 220 to expand, as shown in FIG. 6B. The portion of earplug 200 positioned in first cavity 271 may be effectively shielded from heat such that activation of the foaming agent is limited. Alternatively or in addition, first cavity 271 constrains outer layer 220 and substantially inhibits expansion caused by activation of the foaming agent that would otherwise result in a greater volume and less dense outer layer. Elongate core 210 and outer layer 220 are subsequently cooled and ejected from mold 270. The finished earplug 200 includes a sound attenuating portion 221 formed by the exposed outer layer that could freely expand and a stem portion 222 that was partially constrained in mold 270 during activation of the foaming agent. Due to the constraint of the mold and/or limited activation of the foaming agent, stem portion 222 may have a greater average density and/or a greater hardness than that of sound attenuating portion 221.

Figure 7A:
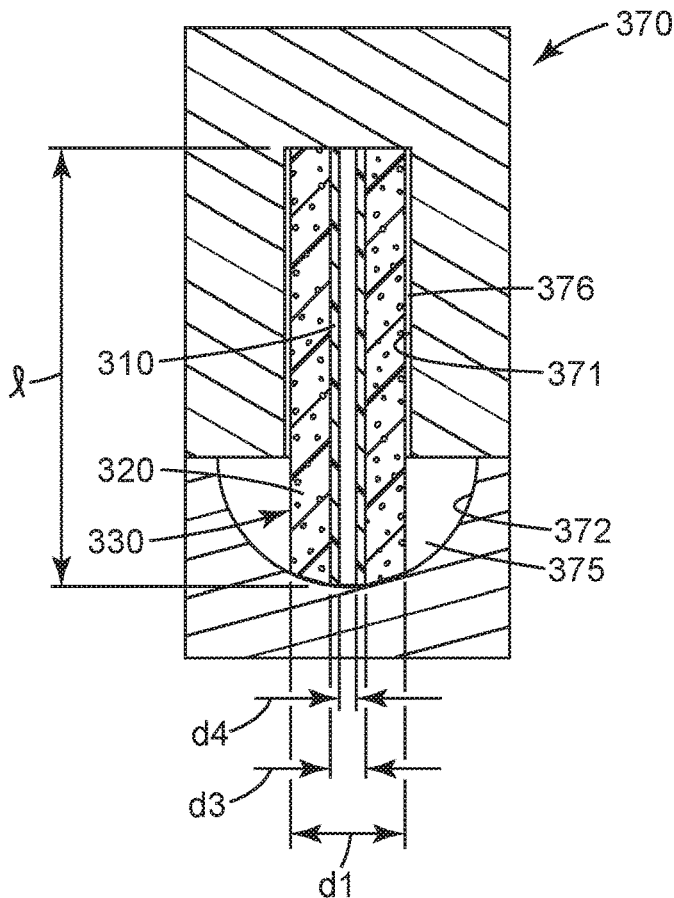
FIGS. 7A and B are cross-sectional views of an example of a mold used in an exemplary embodiment of the present description.
Figure 7B:
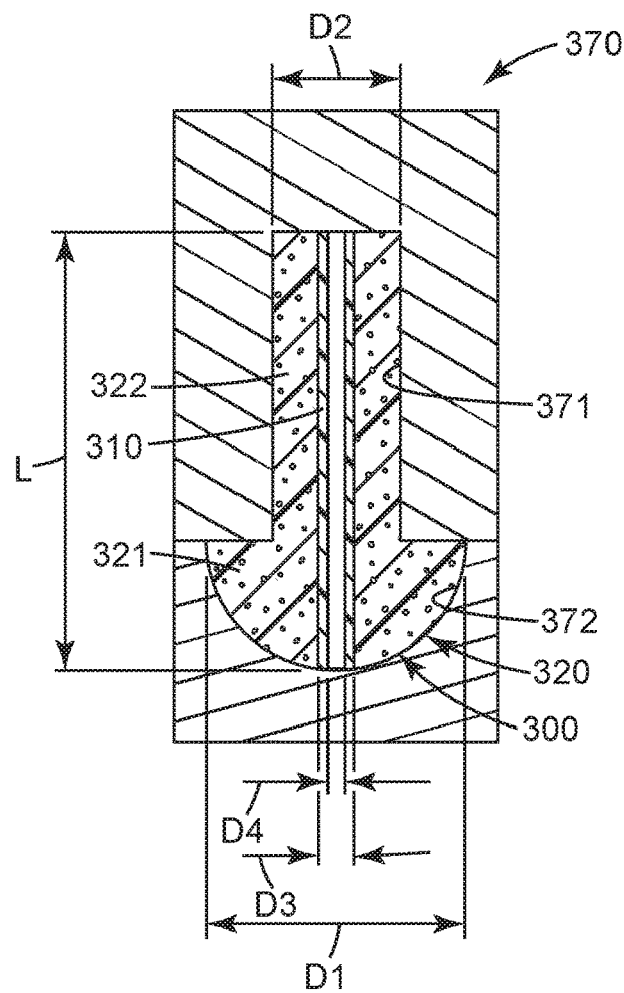

In the exemplary embodiment of FIGS. 7A and 7B, mold 370 is used to control expansion of outer layer 320 of pre-form 330. Mold 370 includes a first cavity 371 in the form of a stem portion that receives a portion of pre-form 330. Mold 370 further includes a second cavity 372 in the form of a sound attenuating portion. When pre-form 330 is initially placed in mold 370, a gap 375 exists between pre-form 330 and a perimeter of second cavity 372. In some embodiments, a small gap 376 may exist between pre-form 330 and a perimeter of first cavity 371. Upon application of heat or other suitable activation source, a portion of outer layer 320 expands to fill gap 375 and substantially conforms to the shape of second cavity 372. The portion of earplug 300 positioned in first cavity 371 may be effectively shielded from heat such that activation of the foaming agent is limited. Alternatively or in addition, expansion of outer layer 220 that would otherwise occur during activation of the foaming agent is constrained by first cavity 371. Further, as application of heat softens outer layer 320 and the foaming agent is activated, outer layer 320 may expand to fill first cavity 371 and some of outer layer 320 initially in first cavity 371 may flow into second cavity 372 to fill gap 375. In an exemplary embodiment, mold 370 includes small gas vents to allow excess gas to escape while preventing passage of any molten material.

In an exemplary embodiment, mold 370 is oriented such that first cavity 371 is oriented above second cavity 372 during a portion or all of the activation process. Such an orientation may allow material to flow from first cavity 371 into second cavity 372 during activation. Further, an orientation in which first cavity 371 is oriented above second cavity 372 may facilitate the formation of an integral skin on sound attenuating portion 321 because cells or gaps formed during activation of the foaming agent may tend to move upward and away from a lower surface of cavity 372.

Earplug 300 is subsequently cooled and ejected from mold 370. Finished earplug 300 includes a sound attenuating portion 321 having the shape of second cavity 372 of mold 370, and a stem portion 322 having the shape of first cavity 371 of mold 370. Due to the constraint of first cavity 371 and/or limited activation of the foaming agent in the area of first cavity 371, stem portion 322 may have a greater average density and/or hardness than that of sound attenuating portion 321.

In the exemplary embodiment shown in FIGS. 7A and 7B, earplug 300 is formed from pre-form 330 having a total length 1 in a longitudinal direction between approximately 15 mm and 40 mm, or of about 25.5 mm. Outer layer 320 has an outer diameter d1 between approximately 2.5 mm and 6.5 mm, or of about 4.5 mm, elongate core 310 has an outer diameter d3 between approximately 1.5 mm and 3.5 mm, or of about 2.5 mm, and channel 315 has a diameter d4 between approximately 1.0 mm and 2.0 mm or of approximately 1.5 mm. After activation of outer layer 320 described above, as shown in FIG. 7B, final earplug 300 has a total length L in a longitudinal direction between approximately 15 mm and 40 mm, or of approximately 25.5 mm, sound attenuating portion 321 has an outer diameter D1 at its widest point between approximately 8 mm and 16 mm, or of approximately 12.5 mm, stem portion 322 has a diameter D2 between approximately 3 mm and 10 mm, or of approximately 6.5 mm, elongate core 310 has an outer diameter D3 between approximately 1.5 mm and 3.5 mm, or of approximately 2.5 mm, and channel 115 has a diameter D4 between approximately 1.0 mm and 2.0 mm, or of approximately 1.5 mm. The dimensions of pre-form 330 and finished earplug 300 can be varied based on the materials of outer layer 320 and elongate core 310, and as required to form a final earplug 300 having desired characteristics for a particular application.

Figure 8:
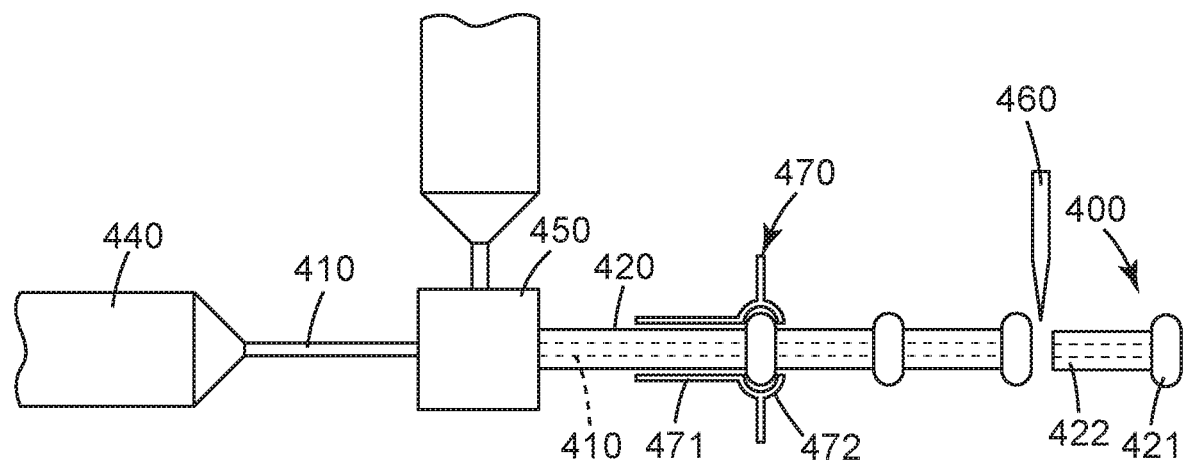
FIG. 8 is a schematic representation of an exemplary manufacturing process according to the present description.

FIG. 8 shows another exemplary method of making an earplug according to the present description. The method includes a step of activating a foaming agent in outer layer 420 prior to cutting the elongate core 410 and outer layer 420 to a desired length. Similar to the method described above with reference to FIG. 5, a first material is extruded through first die 440 and drawn to an appropriate diameter. The extruded and uncut elongate core 410 is cooled and covered, directly or indirectly, with outer layer 420. In an exemplary embodiment, elongate core 410 is covered with outer layer 420 by a second die 450. Alternatively, elongate core 410 can be covered with outer layer 420 by laminating, molding, spraying, dipping or any other suitable process known in the art.

Elongate core 410 and outer layer 420 may be subsequently cooled. Portions of the uncut elongate core 410 and outer layer 420 are then positioned in mold 470 by, for example, bringing two halves of mold 470 together over the uncut elongate core 410 and outer layer 420. With the mold appropriately positioned relative to the uncut elongate core 410 and outer layer 420, the foaming agent is activated by heat or other activation source to cause outer layer 420 to expand. In embodiments in which outer layer 420 includes an uncured or partially cured material, application of heat or other activation source also causes outer layer 420 to cure.

In an exemplary embodiment, mold 470 includes a first cavity 471 in the form of a stem portion and a second cavity 472 in the form of a sound attenuating portion. Upon application of heat or other suitable activation source, a portion of outer layer 420 expands to fill second cavity 472 and substantially conform to the shape of second cavity 472. The portion of earplug 400 positioned in first cavity 471 may be effectively shielded from heat such that activation of the foaming agent is limited. Alternatively or in addition, expansion of outer layer 420 that would otherwise occur during activation of the foaming agent is substantially constrained by first cavity 471. Further, as application of heat softens outer layer 420 and the foaming agent is activated, some of outer layer 420 initially in first cavity 471 may flow into second cavity 472. In an exemplary embodiment, mold 470 includes small gas vents to allow excess gas to escape while preventing passage of any molten material.

Elongate core 410 and activated outer layer 420 are then cooled, removed from mold 470, and cut to a desired length with cutter 460 to result in finished ear plug 400. Finished earplug 400 includes a sound attenuating portion 421 having the shape of second cavity 472, and a stem portion 422. Due to the constraint of first cavity 471 and/or limited activation of the foaming agent in the area of first cavity 471, stem portion 422 may have a greater average density and/or hardness than that of sound attenuating portion 421.

In another exemplary embodiment, only a portion of the uncut elongate core 410 and outer layer 420 are positioned in a mold cavity. The mold cavity may be in the form of a stem such that expansion of a portion of outer layer 420 is substantially constrained to form stem portion 422, while the remaining portion of outer layer 420 may freely expand to form sound attenuating portion 421. Alternatively, the mold cavity may be in the form of a sound attenuating portion such that expansion of a portion of outer layer 420 is constrained and selectively activated to form sound attenuating portion 421, while the remaining portion of outer layer 420 is not activated, or is only partially activated, and forms stem portion 422.

An earplug according to the present description may also be made according to variations of methods described herein and other methods. For example, an exemplary earplug may be made by covering a relatively stiffer elongate core with an outer layer as a foaming agent is activated, or covering a relatively stiffer elongate core with an outer layer that has been previously foamed. The foamed outer layer may be subsequently cut, compressed, densified, or otherwise shaped to form an outer layer having a stem portion and a sound attenuating portion.

An earplug and a method of making an earplug described herein provides several benefits. The earplug described herein may be comfortably positioned in the ear canal of a user to provide a desired level of hearing protection, and the presence of a stiffer elongate core promotes hygiene by eliminating the need to roll down a sound attenuating portion prior to insertion. The method described herein allows an earplug to be efficiently manufactured. An earplug having an outer layer bonded, directly or indirectly, to an elongate core as described herein eliminates the cost and complexity of an additional step of joining a rigid component to a sound attenuating component required of many prior push-in type earplugs. The elongate core and outer layer can be thermally bonded without the need for an additional adhesive or additional assembly step.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures. Any feature or characteristic described with respect to any of the above embodiments can be incorporated individually or in combination with any other feature or characteristic, and are presented in the above order and combinations for clarity only.

What is claimed is:

1. A method of making an article, the method comprising: preparing a preform having a first end portion and a second end portion by:
   extruding a first material and a second material to an extruded form, the second material at least partially covering the first material, the second material comprising a foaming agent having an activation temperature, and the second material having a temperature below the activation temperature; and
   cutting the extruded form to make the preform;
positioning at least a portion of the preform in a mold, wherein the mold comprises a sound-attenuating portion shape and a stem portion shape; and
increasing the temperature of the preform to at least the activation temperature of the foaming agent to activate the foaming agent within the second end portion causing the second material to expand to fill the mold, and wherein when activated, the foaming agent causes the second material to expand into the sound attenuating portion shape, such that the second end portion, when cooled, retains a sound-attenuating portion with the sound-attenuating portion shape, and wherein the first end portion retains the stem portion shape and the second material comprises a thermoset polymer that can take and retain a shape such that the sound-attenuating portion retains the sound-attenuating portion shape after use.

2. The method of claim 1, wherein the second material comprises between 0.5% weight and 3% weight of the unactivated chemical foaming agent.

3. The method of claim 1, wherein an expandable sphere foaming agent comprises between 0.5% weight and 9.5% weight of the second material prior to activation.

4. The method of claim 1, wherein the second material comprises a thermoplastic.

5. The method of claim 1, wherein the second material comprises styrene-ethylene-butylene-styrene (SEBS).

6. The method of claim 1, wherein the second material comprises an EPDM rubber.

7. The method of claim 1, wherein the first material is selected from the group consisting of polypropylene and styrene-ethylene-butylene-styrene (SEBS).

8. The method of claim 1, wherein the second material comprises a foaming agent having an activation temperature between 100° C. and 205° C.

9. The method of claim 1, wherein the second material comprises an outer layer portion of a hearing protection device.

* * * * *